US006328693B1

United States Patent
Miyatake et al.

(10) Patent No.: US 6,328,693 B1
(45) Date of Patent: Dec. 11, 2001

(54) METHOD AND DEVICE OF SYNTHESIZING PANORAMA IMAGE FROM ULTRASOUND IMAGES

(75) Inventors: Takafumi Miyatake, Hachioji; Akio Nagasaka, Kodaira; Shinichiro Umemura, Hachioji, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/492,132

(22) Filed: Jan. 27, 2000

(30) Foreign Application Priority Data

Jan. 28, 1999 (JP) .................................. 11-019462

(51) Int. Cl.[7] ....................................... A61B 8/00
(52) U.S. Cl. ........................................ 600/437; 600/443
(58) Field of Search ................................. 600/437, 443, 600/447, 454–456, 407; 73/625, 626

(56) References Cited

U.S. PATENT DOCUMENTS

| 5,575,286 | 11/1996 | Weng et al. . | |
|---|---|---|---|
| 5,782,766 | * 7/1998 | Weng et al. | 600/443 |
| 6,117,081 | * 9/2000 | Jago et al. | 600/443 |
| 6,159,152 | * 12/2000 | Sumanaweera et al. | 600/443 |

* cited by examiner

Primary Examiner—Marvin M. Lateef
Assistant Examiner—Ali M. Imam
(74) Attorney, Agent, or Firm—Mattingly, Stanger & Malur, P.C.

(57) ABSTRACT

A cheap, very operable ultrasound diagnosing device capable of forming a panorama slice image in a real time manner is realized. The device comprises: an imaging unit 120 for converting ultrasound data obtained from a probe 200 into an image; computers (130, 140) having a shift amount detecting function of detecting a shift amount between formed images by the operation of the probe 200 and a rotation amount detecting function of detecting a rotation amount between slice images generated by the operation of the probe 200; and panorama image displaying means 150 for displaying a panorama image 151 obtained by connecting the sequence of slice images captured during diagnosis in a plane manner in accordance with the shift amount and the rotation amount detected by the computers in parallel to the motion image display. Thus, the panorama image can be formed in a real time manner from the sequence of slice images obtained by the probe. The panorama image forming state can be recognized on a display momentarily and an erroneous probe operation can be corrected.

20 Claims, 10 Drawing Sheets dx : SHIFT VECTOR BETWEEN IMAGE It AND It+1
dΘ : ROTATION VECTOR BETWEEN IMAGE It AND It+1

METHOD AND DEVICE OF SYNTHESIZING PANORAMA IMAGE FROM ULTRASOUND IMAGES

BCACKGROUND OF THE INVENTION

The present invention relates to a method and device of synthesizing a panorama image from motion images obtained by ultrasound waves and, more particularly, to a method and device of obtaining an image (hereinbelow, called a panorama image) by synthesis of a sequence of consecutive frame images which are captured in a position by a manual ultrasound probe operation, which is especially suitable for an ultrasound diagnosis and a device used for the ultrasound diagnosis.

In recent years, a diagnosis using ultrasound waves is becoming widespread. According to the ultrasound diagnosing device, a probe is manipulated on the surface of a subject such as human body while generating ultrasound waves of 2 to 10 MHz that travel into the body, the ultrasound waves reflected by the surface of internal organs or the like are received, the received ultrasound waves are subjected to signal processing, and slice images of the organs or the like of the patient are real-time displayed. The diagnosis using ultrasound waves does not give pain or adverse influence on the patient and is safer as compared with a surgical operation or a diagnosis using X-ray. Consequently, it is important in diagnosing a pregnant woman and an infant. Representative measurement examples of the ultrasound diagnosing device are growth measurement of an unborn baby and circulatory organ measurement. Since their measurement regions are larger than the range in which a slice image can be displayed by using the probe at once, the function of obtaining a panorama image from the slice images and displaying the panorama image while scanning the subject with the probe is necessary. Although only a two-dimensional cross sectional image of an extremely narrow range can be obtained by one capturing operation, when the probe is attached to a mechanical scanner having a position sensor and slice images are stored while shifting the scanner across the human body, a panorama image of the whole can be produced from all of the stored slice images when the manipulation of the probe on the subject such as human body is finished.

SUMMARY OF THE INVENTION

It is, however, difficult to accurately shift the probe attached to the mechanical scanner along a curved region of the human body such as the calf or the thyroid gland. Since the ultrasound waves are transmitted into the body through a layer of a jelly material applied on the skin, the probe has to be held so as to be in direct contact with the skin of the human body. A high-degree operating technique is therefore necessary to accurately scan a part having a curved surface. It is desirable to realize a device capable of synthesizing a panorama image by connecting cross sectional images over a wide range in a real time manner and displaying the panorama image while manually scanning the surface of the human body with the probe. In order to synthesize images without using a position sensor or rotation sensor, a shift amount and a rotation amount between frame images which are neighboring with respect to position have to be detected from image data. For the detection, a motion vector between images has to be calculated. For the real-time processing, a high-speed image processor is required.

Further, in order to improve the operability of the device of obtaining an ultrasound slice image, a function capable of producing a panorama image only by correcting an operation partly is necessary even when a wrong region is scanned by a manual probe operation of the user of the diagnosing device. For example, in the case of measuring the bloodstream, the user has to move the probe along the blood vessel on the surface of the human body. Since the blood vessel is narrow, however, there is a case such that the position of the probe is deviated from the position of the blood vessel to be measured. In such a case, when the operation of the probe is not restarted but can be corrected and the scanning can be restarted, the operability is certainly improved. When means by which the user can check the slice image while shifting (scanning with) the probe without turning his/her eyes from the probe position is provided, accurate scanning operation can be made possible.

Realization of a desired ultrasound diagnosing device has, however, a problem such that the cost of the device is very high since the mechanical scanner to which the position sensor is attached, a high-speed image processor, or the like is necessary.

U.S. Pat. No. 5,575,286 discloses a panorama image generating technique for use in an ultrasound diagnosing device, for obtaining a panorama image by deriving a motion vector between ultrasound image frames which are related to each other and connecting a plurality of frame images by using the motion vector. Since the technique disclosed in the above uses what is called advanced block matching to obtain the motion vector, however, a signal processing amount is still large. There is a problem such that a high speed signal processor is necessary to perform a real-time process.

Although the conventional ultrasound diagnosing device is safe to the human body, there are problems of the high cost of the device and the low operability in the case of displaying a panorama image of the whole. Specifically, there are problems such that a high-speed image processor is necessary to obtain the panorama image of the human body from partial cross-sectional images and the panorama image is discontinued when the probe is not moved accurately.

It is therefore an object of the invention to provide a panorama image synthesizing method capable of generating and real-time displaying a panorama image from ultrasound images of the subject and a cheap, easily operable ultrasound diagnosing device of carrying out the method.

In order to achieve the object, there is provided a method of synthesizing a panorama image from ultrasound images, comprising the steps of: obtaining image data of a plurality of frame images which are time-sequential derived by ultrasound waves returned from the subject such as a human body, detecting positional relation data between neighboring frame images, that is, a shift amount and a rotation amount between the frame images from data in each of specific designated areas of the plurality of frame images, and connecting the plurality of frame images in a predetermined position. As necessary, the panorama image data is converted into an image signal and the image signal is displayed on a display.

The method of the invention also includes not only a mode of directly obtaining the positional relation data from motion image data captured from the probe, obtaining panorama image data, and real-time displaying the panorama image on the display simultaneously with the movement of the probe but also a mode of storing data of the plurality of frame images into storing means, obtaining the panorama image data from the data in the storing means after elapse of some time, and displaying the panorama image data on display means.

An image synthesizing device for synthesizing a panorama image according to the invention comprises: means for inputting a plurality of frame images which are neighboring with respect to position; motion detecting means for detecting positional relation data between the frame images, that is, a shift amount and a rotation amount between the frame images from data in a specific area of the plurality of frame images; a signal processor for obtaining panorama image data by connecting the plurality of frame images in a predetermined position by using the shift amount and the rotation amount; and a display device for displaying the panorama image data. The motion detecting means has calculating means for performing the following processes.

The calculating means has: signal processing means for obtaining the shift amount by deriving a projective distribution in a single designated specific area in consecutive frame images and correlating the projective distributions in the single specific area between neighboring frame images; and signal processing means for deriving a projective distribution in each of a plurality of specific partial areas divided in one axis direction of each of consecutive frame images, correlating the corresponding projective distributions between neighboring frame images, thereby obtaining the shift amount in each of the specific partial areas, and obtaining the rotation amount data of consecutive frame images from a difference between the shift amounts in the plurality of specific partial areas. That is, the movement of the probe operation is detected from image data.

In a panorama image synthesizing device of the invention, in a preferred embodiment, means for obtaining the plurality of frame images is ultrasound imaging means for converting ultrasound data captured by a manually operated probe into image data. The display device displays the panorama image and simultaneously displays the plurality of frame images as a motion image.

In a preferred embodiment of the panorama image synthesizing device according to the invention, each of the motion detecting means and the panorama image synthesizing means is realized by a computer having a central processing unit (CPU) and a memory for storing data and a control program. Further, image storing means for storing the panorama image is also provided.

According to a preferred embodiment for further increasing the operability, the probe is provided with at least one of operation start means, operation reset means, the motion image displaying means, and panorama image displaying means.

Other objects and features of the invention will appear more fully from the following description. Since the invention is especially effective on an ultrasound diagnosing device, the ultrasound diagnosing device will be described hereinbelow but the invention can be also carried out for other applications.

BRIEF DESCRIPTION OF THE INVENTION

DESCRIPTION OF THE PREFERRED EMBODIMENTS

Figure 1:
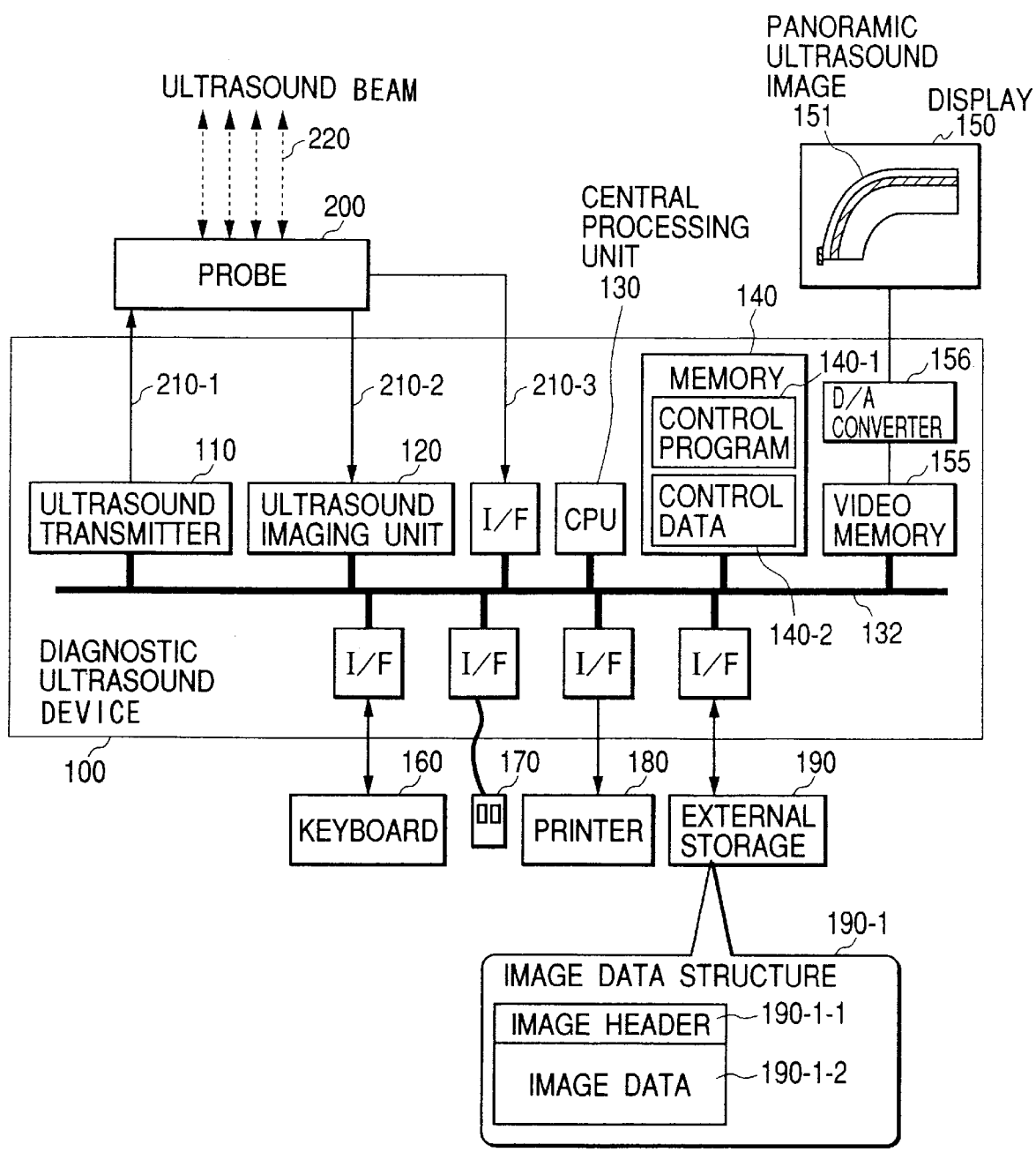
FIG. 1 is a block diagram showing the configuration of an ultrasound diagnosing device as an embodiment of a device of synthesizing a panorama image from ultrasound images according to the invention.

FIG. 1 is a block diagram showing the configuration of an ultrasound diagnosing device as an embodiment of the device of synthesizing a panorama image from ultrasound images according to the invention.

In the embodiment, an ultrasound diagnosing device 100 comprises: a probe 200 for emitting an ultrasound beam 220 to the subject by a signal from an ultrasound transmitter 110 and receiving a beam reflected from the subject; an ultrasound imaging unit 120 for converting a signal from the probe 200 into a frame image; a central processing unit (hereinbelow, abbreviated as CPU) 130 for processing motion image data; a memory 140 for storing data 140-2 necessary to process a motion image and a panorama image and a control program 140-1; an image memory 155 for displaying a panorama image 151 or the like on a display 150; a D/A converter 156; and a bus line 132 for connecting the functioning units. The ultrasound diagnosing device 100 has input/output devices such as a keyboard 160 and a pointing device 170 connected via an interface (I/F), a printer 180, and an external storage 190. The hardware structure of the ultrasound diagnosing device 100 is similar to that of a generally known digital computer.

In the configuration of the device, the oscillation frequency (2–10 MHz) of the ultrasound transmitter 110 follows an instruction from the CPU 130. Image data converted by the ultrasound imaging unit 120 is stored into the memory 140 and simultaneously into the image memory 155. The image data written in the image memory 155 is sequentially read by the D/A converter 156 called an RAMADC in accordance with a scanning speed of the display 150 and is displayed on the display 150.

When the data of the image memory 155 is updated, the updated data is therefore immediately reflected on the image displayed on the display 150. The display 150 is a device for displaying an image. For example, a small CRT or plasma display, a liquid crystal display, or the like is used. By repeating the capture of an image at the frequency of about 30 times per second, motion images as consecutive slice images of the subject are displayed on a part of the display.

The external storage 190 is a large-capacity recording device such as a hard disk for semipermanently storing digital data. This can be a recording device such as a PCMCIA type hard disk card which can be detached from the body 100 or a recording device of a type from which only a recording medium such as a magnetooptic disk can be detached.

The CPU 130 executes a control program for performing a control for ultrasound diagnosis, obtaining image data which will be described hereinlater, detecting a motion in images, converting image data into an image display signal, or controlling a display format of an image. The control program stays resident on the memory 140-1 and data necessary to execute the program is stored in the data memory 140-2 as necessary. The printer 180 prints a processed image or diagnostic result.

In the configuration of the ultrasound diagnosing device, the frame images in the captured sequence of frame images are connected to each other in accordance with a shifting operation (hereinbelow, also called scanning) of the probe 200. According to the control program stored in the memory 140-1, while storing the image data captured during diagnosis into the memory 140, designated frame images in the plurality of frame images are connected to thereby obtain panorama image data, the panorama image data is sequentially transferred to the image memory 155 and the panorama image 151 is displayed on the display 150. When the diagnosis is finished, the panorama image data is stored as an image data structure 190-1 in the external storage 190. The image data structure 190-1 includes an image header 190-1-1 such as the type and size of the image, date and time of diagnosis, and region of diagnosis, and panorama image data 190-1-2 compressed or not compressed.

Figure 2:
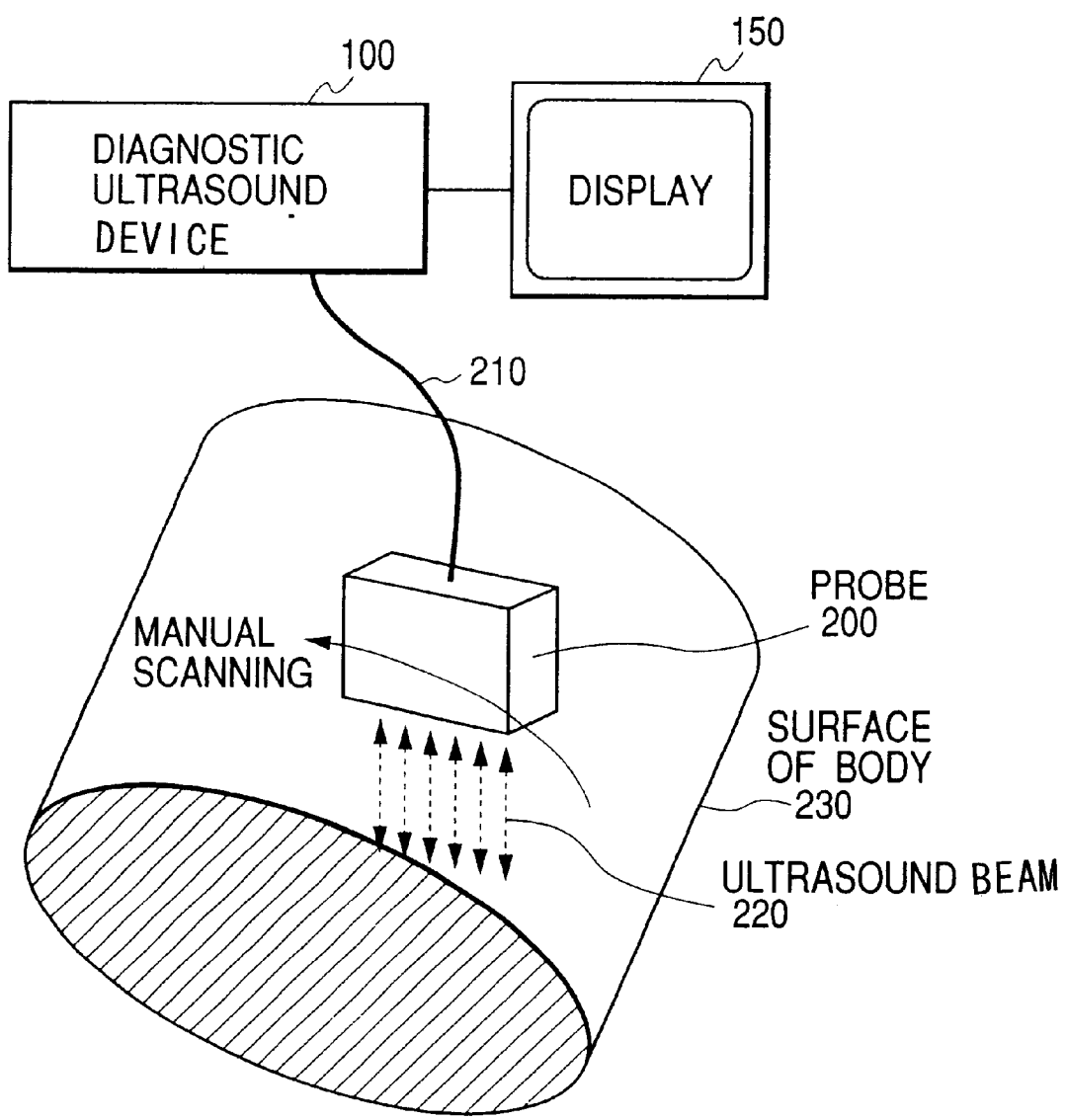
FIG. 2 is a schematic diagram for explaining an embodiment of the ultrasound diagnosing device according to the invention.

FIG. 2 is a schematic diagram for explaining an embodiment of the ultrasound diagnosing device according to the invention. The probe 200 is manually shifted in the longitudinal direction (shown by a curve with an arrow) of the probe 200 along the surface 230 of the body (a part of the subject). Most pixels of time-sequential frame images obtained by shifting the probe 200 coincide with each other. As will be described in relation to FIG. 6, a positional deviation occurs between the images in correspondence with the shift distance in the moving direction of the probe. A rotational deviation occurs between the images in accordance with the curvature of the body surface 230. According to the ultrasound diagnosing device 100 of the embodiment, the shift amount and the rotation amount between the frame images are detected by a signal process of calculating means constructed by the CPU 130 and the program 140-1. By using the detected shift amount and rotation amount, the plurality of frame images are synthesized into panorama image data which is sequentially displayed as the panorama image 151 via the image memory 155 on the display 150. Consequently, a panorama image synthesizing device easy to operate is realized without using a position sensor.

Figure 3:
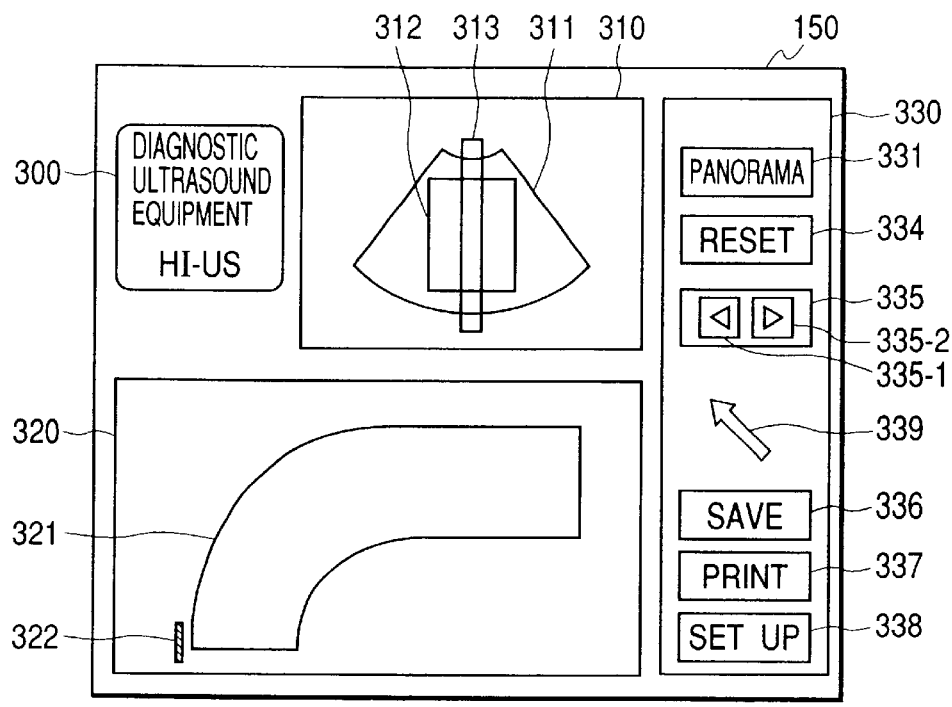
FIG. 3 is a diagram showing an example of a screen displayed on a display of the ultrasound diagnosing device in the embodiment.

FIG. 3 is a diagram showing an example of a screen displayed on the display of the ultrasound diagnosing device in the embodiment.

The display 150 comprises a trademark window 300, a motion image display window 310, a panorama image display window 320, and an operation instruction window 330. In the trademark window 300, the device name, the holder of the copyright, and the like are displayed. In the motion image display window 310, slice images obtained during medical examination are displayed in a real time manner. By displaying images at the frequency of 30 frames per second, the state of the internal of the body is displayed as motion images. An area 311 in the motion image display window 310 is an effective area of the slice image. When the shape of the probe 200 for transmitting and receiving the ultrasound beam 220 is a convex type, the effective area of the slice image (frame image) has a fan shape as shown in the diagram. In the diagram, the upper part corresponds to the body surface side and the lower part corresponds to the inside of the body. When the shape of the probe 200 is a linear type, the effective area 311 has a rectangle shape.

An area 312 is an image processing area which is set in the slice image 311 and used to form a panorama image. The area 312 is displayed as a rectangle figure. The image data signal process of detecting the motion amount and the rotation amount between close frame images is performed by using the data in the area 312. The process area 312 is usually fixed with respect to the effective area 311. Since there is a case such that the size and position of a captured image change when the probe 200 is replaced, the process area is changed accordingly.

An area 313 is a partial area of a slice image used to form a panorama image. The partial area 313 is an area of a motion image having high resolution. Frames are set in the same position. The user can freely set the image processing areas 312 and 313 via a user interface.

In the panorama image display window 320, the whole panorama image formed in a real time manner from slice images captured during diagnosis is displayed. An area 321 denotes a panorama image. An area 322 denotes a cursor indicating the position and direction of the probe 200 presently being operated.

There is a case that the panorama image 321 is larger than the panorama display window 320 depending on the shift distance of the probe 200. In this case, it can be solved by scaling and displaying the panorama image 321 so as to be within the panorama image display window 320.

The operation instruction window 330 is used to instruct an operation necessary for diagnosis and has a button 331 for instructing panorama image display, a reset button 334, an operation correction button 335, a save button 336, a print button 337, and a setup button 338. The button selection is carried out by moving a pointer 339 by the pointing device 170 such as a mouse onto a desired button and clicking the pointing device 170. It is also possible to attach a touch panel on the display 150 and directly push a desired button with a finger. The panorama image 321 in FIG. 3 shows the final result of the diagnosis.

FIGS. 4A to 4D show panorama images on the panorama image display window 320 in the embodiment. An operation in a diagnosing process of the ultrasound diagnosing device according to the invention and the panorama display image will be described with reference to FIG. 3 and FIGS. 4A to 4D. An ultrasound diagnosis is started by pushing the panorama button 331 in FIG. 3. When the panorama button 331 is pushed, an image displayed on the panorama image display window 320 is cleared. From the state, as the probe 200 is manipulated along the body surface 230, panorama images are sequentially formed.

Figure 4A:
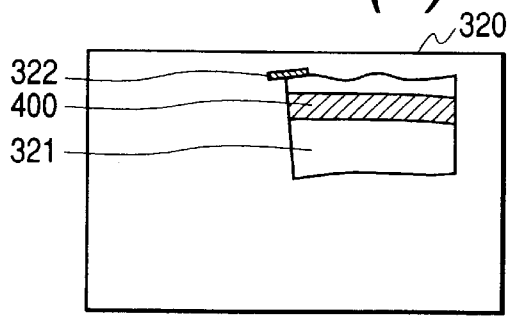
FIGS. 4A to 4D are diagrams showing panorama images each displayed on a panorama image display window in the embodiment.
Figure 4B:
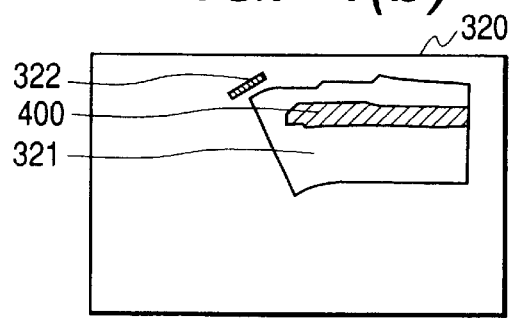

FIG. 4A shows a panorama image obtained when the probe 200 is scanning a blood vessel. FIG. 4B shows an example in which a blood vessel image 400 is cut since the position of the probe is deviated from the blood vessel.

When the panorama button 331 is pushed in such a state, the panorama image formation is interrupted. In the state, the user corrects the position of the probe 200 by seeing the image on the motion image display window 310 so that the image 400 of the blood vessel is displayed. After that, when the panorama button 331 is pushed, the panorama image forming process is restarted. When the interruption in the image 400 of the blood vessel is large, it is necessary to return a panorama image to a previous state. In this case, the operation correction button 335 is used. The correction button 335-1 is a button to return the panorama image to a previous state. When the correction button 335-1 is continuously pushed, the cursor 322 sequentially goes back to previous states. A button 335-2 is a button to advance the cursor which has returned too much.

Figure 4C:
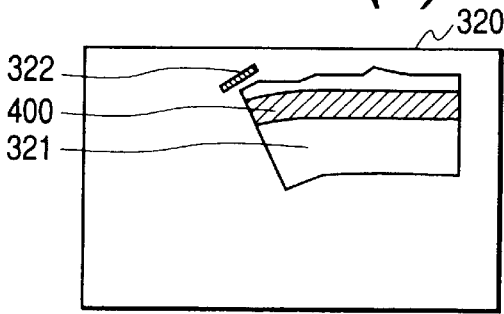
Figure 4D:
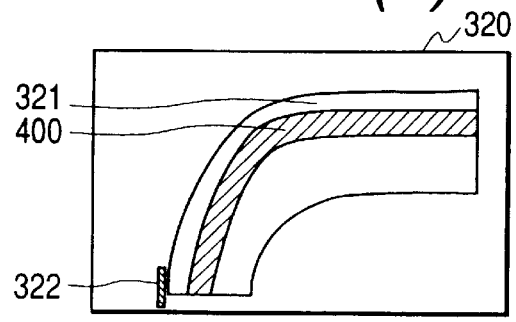

FIG. 4C shows an example in which the process is restarted and the blood vessel image 400 is continued. FIG. 4D is an example of a panorama image finally obtained. When the reset button 334 is pushed during the panorama image formation, the panorama image display window 320 enters the initial diagnostic state and the panorama image 321 is cleared.

According to the embodiment as mentioned above, the user can freely correct a panorama image during diagnosis or restart the panorama image forming process, so that an easily operable ultrasound diagnosing device is realized. Further, the result can be easily saved or printed. When the save button 336 is pushed, the panorama image is stored in the external storage 190. By pushing the print button 337, the panorama image can be printed by the printer 180. The setup button 338 is used to input various information necessary for setting up the image processing areas 312 and 313 or diagnosis.

Figure 5:
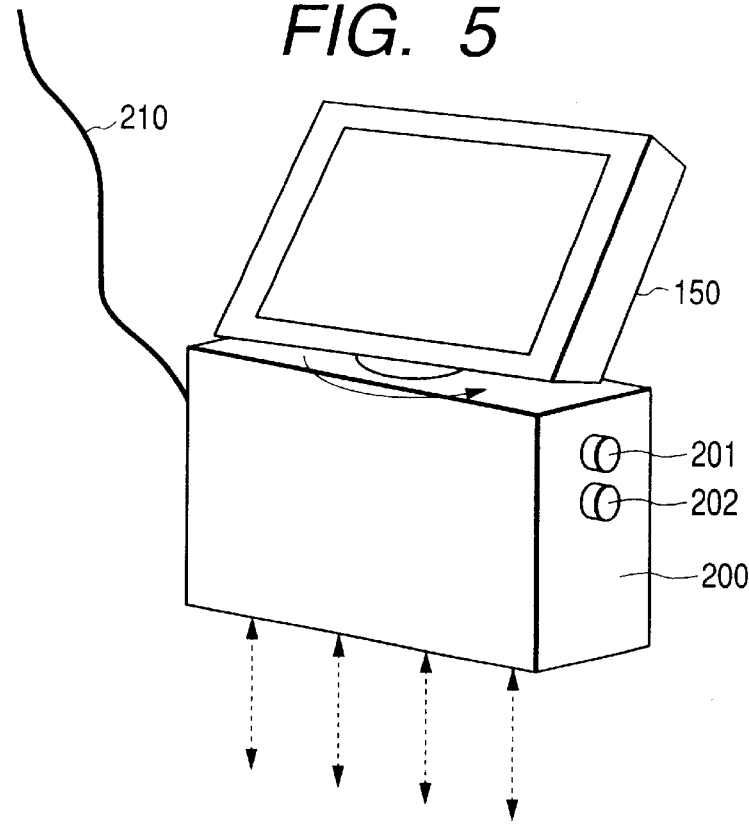
FIG. 5 is an external view of a probe used in another embodiment of the ultrasound diagnosing device according to the invention.

FIG. 5 is an external view of a probe used in another embodiment of the ultrasound diagnosing device according to the invention. In the embodiment, in order to make diagnosis easier, the probe 200 and the liquid crystal display 150 are integrally formed. Specifically, the liquid crystal display 150 is rotatably attached to a part of the body of the probe 200. The probe 200 is provided with buttons 201 and 202 having the functions equivalent to those of the panorama button 331 and the reset button 332 shown in FIG. 4, respectively. In the embodiment, by the buttons 201 and 202 provided for the probe 200 on hand, restart and interruption of the diagnosis can be executed. Since the user does not have to turn his/her eyes off from the probe 200 during the diagnosis, the diagnosis can be easily and accurately performed.

Figure 6:
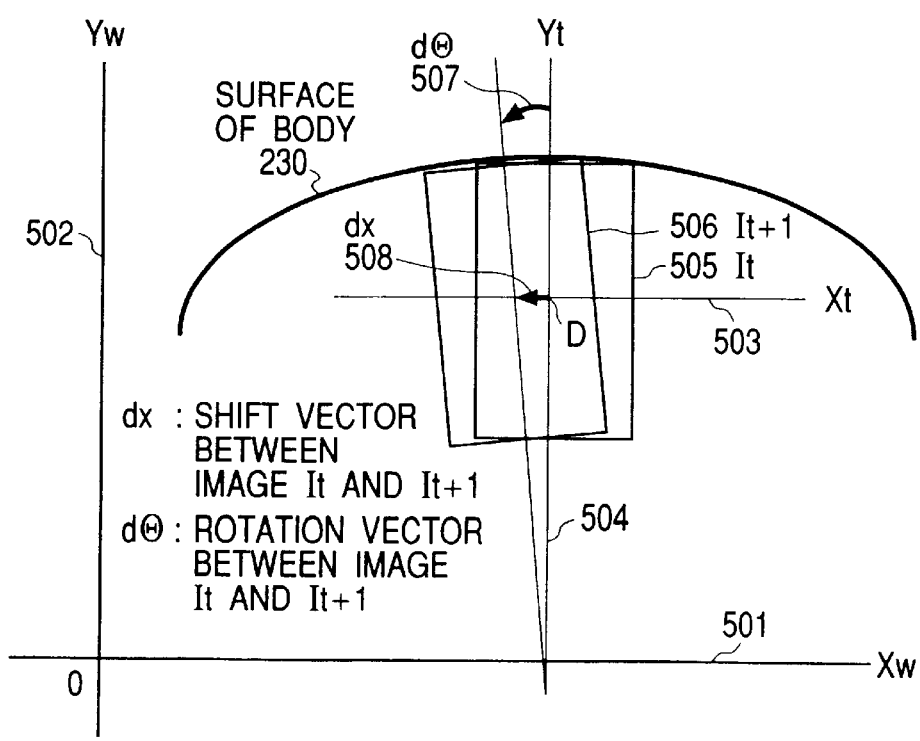
FIG. 6 is a diagram showing a geometric relation between time-sequential frame images obtained by the probe of the ultrasound diagnosing device according to the invention.

FIG. 6 shows a geometric relation between time-sequential frame images obtained by the probe of the ultrasound diagnosing device according to the invention. In the diagram, the curvature 230 denotes the body surface, a slice image It obtained at time t is displayed in an image area 505 and a slice image It+1 obtained at time t+1 is displayed in an image area 506. Since the body surface 230 is a curve, the images It and It+1 have a geometric relation of shift and rotation as shown in the diagram. More specifically, in the case of a coordinate system in which the center (o) of the area 506 of the image It is used as an origin, the lateral axis 503 of the image It is set as Xt axis and the axis 504 which perpendicularly crosses the Xt axis is set as a Yt axis, the image It+1 moves by dx 508 along the X axis and is turned by dΘ 507 around the origin (o). From the shift amount dx and the rotation amount dΘ, the geometric relation between close frame images can be expressed by the following expression.

$$p'=Ap+B$$

where A denotes a rotation matrix, B denotes a shift amount, p indicates coordinates of the image It, and p' expresses coordinates of the image It+1.

Figure 7:
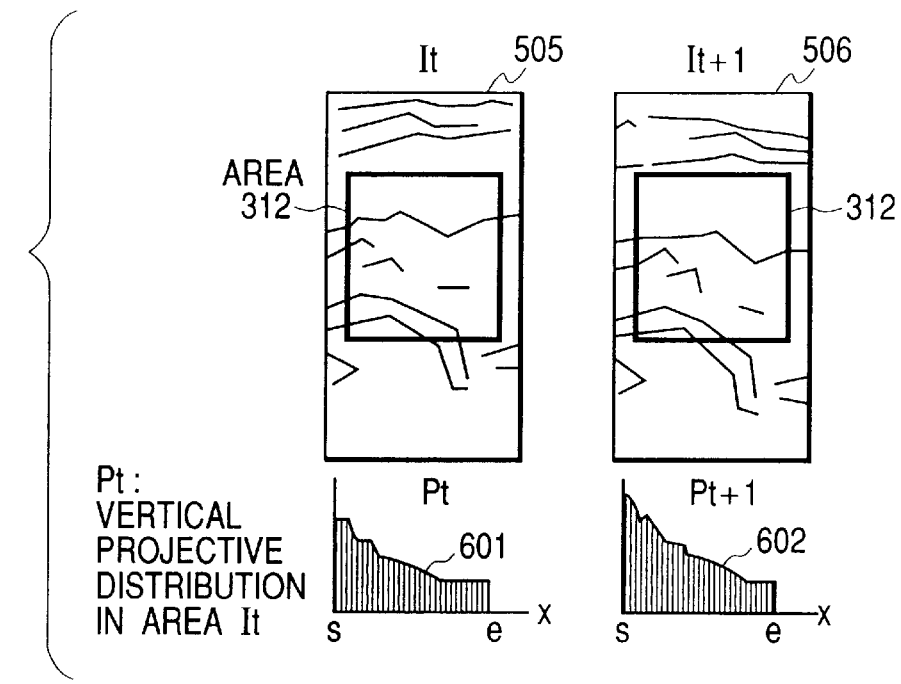
FIG. 7 is a diagram for explaining the principle of the shift amount detection in an embodiment of the panorama image synthesizing device according to the invention.

FIG. 7 is a diagram for explaining the principle of the shift amount detection in the embodiment of the panorama image synthesizing device according to the invention. In the diagram, line segments, polygonal lines, and the like (blood vessel or the like) in the image It in the image area 505 and the image It+1 in the image area 506 show an image. The area 312 in each of the image areas 505 and 506 is the image processing area used to form the panorama image. The shift amount dx between the image It and the image It+1 is detected as follows. Vertical projective distributions 601 and 602 in the image area 312 of the images are obtained. After that, the projective distributions are correlated. While shifting the position in the horizontal direction, the position where the correlation value E(dx) shown hereinbelow becomes the minimum is obtained as a shift amount dx. The correlation value E(dx) is the sum of difference absolute values of the values of the elements between the projection distributions and is expressed by the following equation.

$$E(dx) = \sum_{i=s}^{e} |Pt(i-dx) - Pt+1(i)| \quad (1)$$

where, e and s denote x coordinates and Pt denotes an amplitude of the projective distribution.

Since a global characteristic amount called a projective distribution in one axis direction of a two-dimensional image is used for calculation of the image shift amount, a motion amount is obtained stably and the calculation amount is extremely small. Consequently, the shift amount can be real-time detected by the ability of an ordinary CPU 130.

Figure 8:
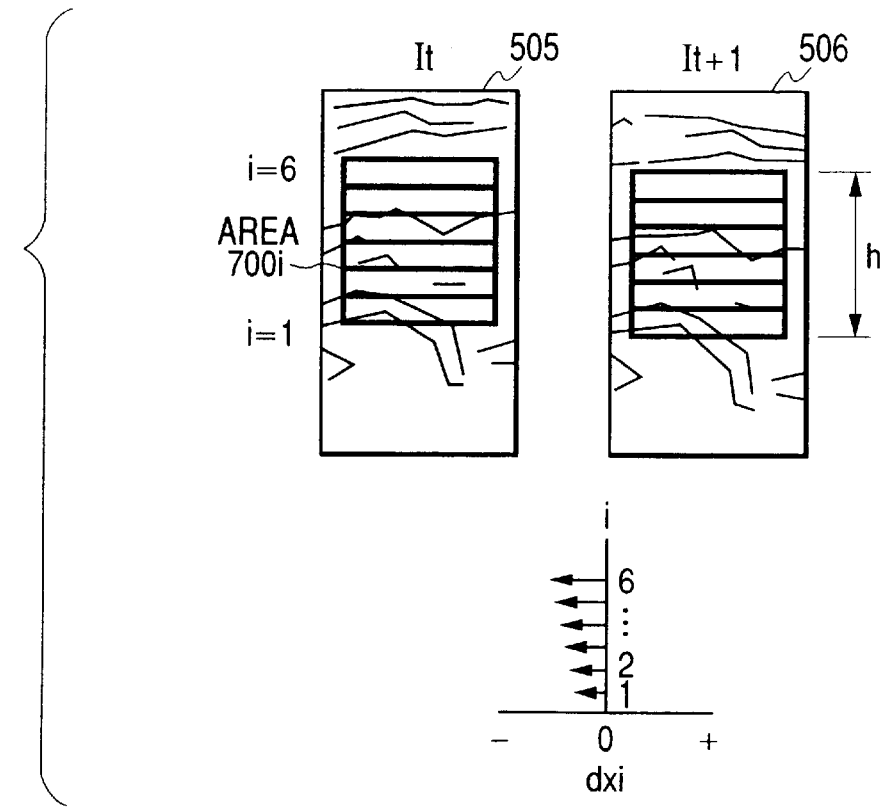
FIG. 8 is a diagram for explaining the principle of the rotation amount detection in the embodiment of the panorama image synthesizing device according to the invention.

FIG. 8 is a diagram for explaining the principle of detection of the rotation amount in an embodiment of the diagnosing device according to the invention. In the diagram, images in image areas 505 and 506 are the same as those in FIG. 7. Although one image process area 312 is sufficient to detect the shift amount, in the case of detecting the rotation amount, one area is insufficient and two or more areas have to be set. FIG. 8 shows an example where six designated partial areas 700i (i=1 . . . 6) are set in order in the vertical direction. The i numbers from 1 to 6 are allocated to the image process areas from the bottom. A projective distribution is obtained every partial area 700i and a shift amount dxi is calculated. When there is a rotation between images, as a principle, the shift vector of each area monotonously increases or decreases as shown in the lower part of FIG. 8 in accordance with the order of i numbers. The rotation amount dΘ is calculated by the equation of the rotation amount dΘ shown below from the difference between the shift amounts in the areas which are most apart from each other.

$$d\Theta = \tan^{-1} \frac{dx6 - dx1}{hx5/6} \quad (2)$$

where, dx6 and dx1 denote shift amounts in the partial areas 7006 and 7001, respectively, and hx denotes the distance in the vertical direction between the areas 7006 and 7001. Since the partial area 700i used to detect the shift amount is set locally, the reliability of the shift amount detection is lower than that shown in FIG. 7. For example, when the probe 200 is moved and comes across a bone or the like, since ultrasound does not penetrate the bone, no echo is returned from the part behind the bone. In an obtained slice image, therefore, the part behind the bone is dark. When the dark part largely occupies each image process area, the shift amount cannot be accurately derived. In the embodiment, pixels are evaluated in each area 700i. When there are many dark pixels, the shift amount detection is not performed. In order to check the reliability of the detected shift amount, the monotonous increase or monotonous decrease in each shift amount is checked in the areas in accordance with the order of the i numbers. Only when the monotony is recognized, the rotation amount is calculated. At this time, the rotation amount is calculated by using a differential value of the shift amounts determined in the partial areas which are most apart from each other.

According to the embodiment, a plurality of partial areas are set for the calculation to detect the rotation amount of an image. Even when a situation such that the shift amount cannot be detected partly occurs, the rotation amount can be calculated from the shift amounts obtained from the other image process areas, so that the reliability is increased. In the embodiment, six partial areas are set. Even when the rotation amount cannot be detected from four out of six areas, it can be detected from the rest of two areas, so that the detection ratio is high. Since the calculation amount is extremely small, the rotation amount can be detected in a real time manner by the ordinary CPU processing ability.

Figure 9:
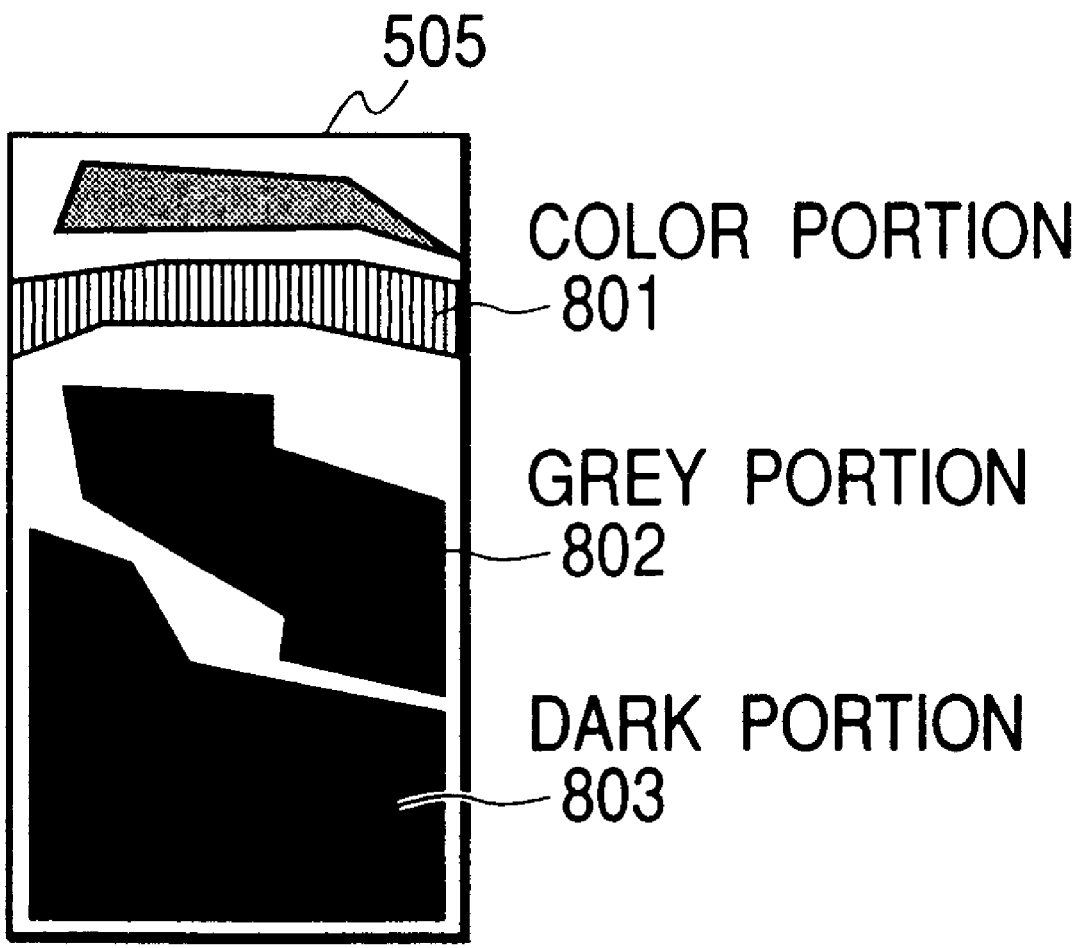
FIG. 9 is a diagram showing an example of an ultrasound slice image.

FIG. 9 shows an example of an ultrasound slice image. The upper part of a slice image area 505 corresponds to the body surface 230 side, that is, the side in contact with the probe 200. A color portion 801 is a portion where the bloodstream is measured in the blood vessel and is especially colored by a color Doppler method. A gray portion 802 is a portion where echoes of ultrasound pulses are returned. A dark portion 803 is a portion where echoes of ultrasound pulses are no returned. When the ultrasound beam 220 are generated and come across a bone or cavity, a dark part occurs. In the embodiment, in the case of detecting the shift amount or rotation amount, only the gray portion 802 is regarded as effective pixels by using a color filter and is subjected to a process, thereby preventing deterioration in the detection accuracy.

Figure 10:
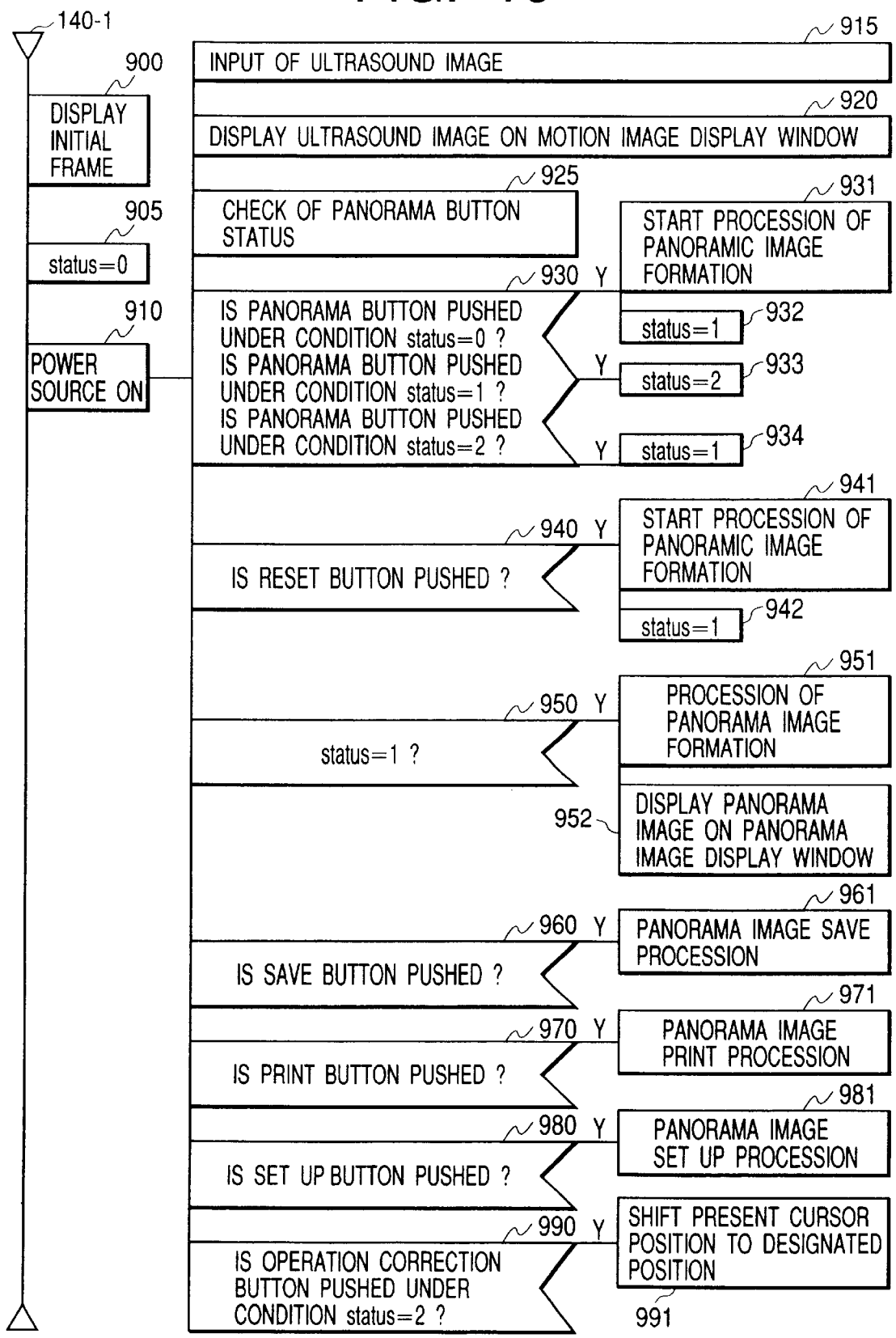
FIG. 10 is a flowchart of an example of a control program of the ultrasound diagnosing device according to the invention.

FIG. 10 is a flowchart of an embodiment of the control program of the ultrasound diagnosing device according to the invention, which mainly shows a panorama image forming process during diagnosis. Besides the panorama image forming process, there are processes such as a control of ultrasound oscillation, display of a diagnosed region in figure, and search of an image. Since the processes are similar to those performed by a conventionally known ultrasound diagnosing device for obtaining a motion image, the detailed description is omitted here. The control program 140-1 in FIG. 10 is executed with reference to the control data 140-2 shown in FIGS. 11 and 12. All of an input image memory, a panorama pixel memory, X_Proj_Current, X_Proj_Last, Rotate_Proj_Current, Rotate_Count_Current, Rotate_Proj_Last, Rotate_Count_Last, Total_dx, Total_dΘ, and k denote memory areas provided in the data memory 140-2.

In FIG. 10, step 900 relates to an initializing process. An initial frame of the ultrasound diagnosing device is displayed on the display 150. In step 905, a variable "status" is reset to 0. When the power source of the ultrasound diagnosing device is on (step 910), the following panorama image forming process is performed.

First, in step 915, signals of an image frame of an ultrasound image, that is, a motion image are captured and stored in a plane input image memory 140-2-1. The input image memory 140-2-1 exists in the memory 140 in FIG. 1.

Figure 11:
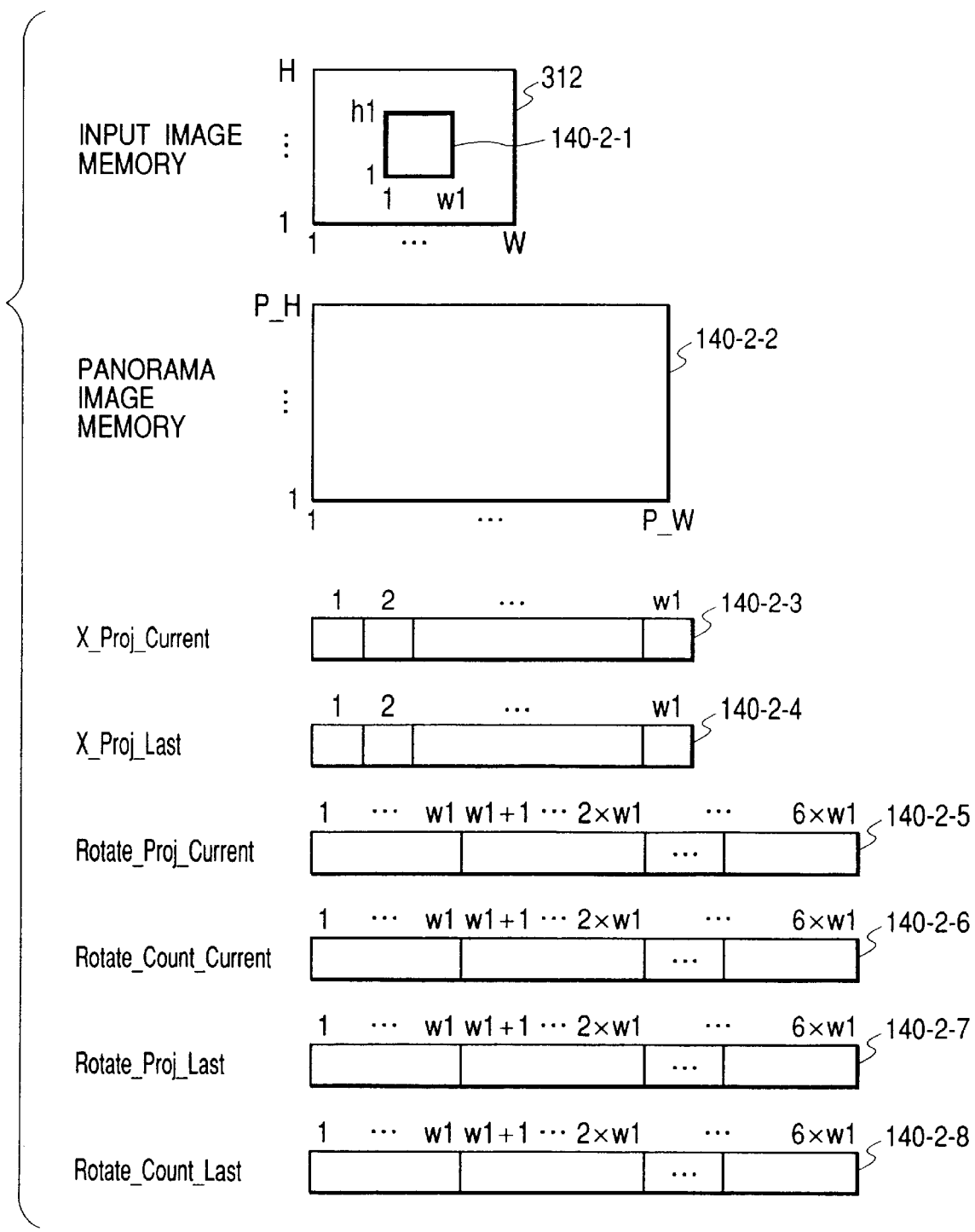
FIG. 11 is a diagram for explaining the structure of control data referred to by the control program executed in the panorama image synthesizing method of the invention.

As shown in the input image memory in FIG. 11, data having a height of 1 to H and a width of 1 to W is stored. The ultrasound image in this area is displayed on the motion image display window 310 of the display 150 (step 920). In step 925, whether the panorama button 331 is pushed or not is checked. The following determining process is performed in step 930.

When the panorama button 331 is pushed under the condition that "status" is 0, a panorama image formation starting process 931 is executed. In the process, a previous panorama image displayed on the panorama image display window 320 is cleared so as to prepare to display a new panorama image. The details of the process 931 will be described hereinlater with reference to FIG. 13. In step 932, the variable "status" is set to 1, thereby setting a panorama image forming mode.

When the panorama button 331 is pushed under the condition that the variable "status" is 1, the variable "status" is set to 2 in step 933 to interrupt the panorama image formation.

When the panorama button 331 is pushed under the condition that the variable "status" is 2, the variable "status" is set to 1 to restart the panorama image formation.

Whether the reset button 334 is pushed or not is checked in the determining process of step 940. When YES, the panorama image formation starting process which has been already described is performed in step 941 and 1 is set in the variable "status" in step 942, thereby setting the panorama image forming mode.

Whether the panorama image is being formed or not is checked in step 950. When the variable "status" is 1, the panorama image is being formed, the panorama image forming process is performed in step 951 and the result is stored in a panorama image memory 140-2-2. The panorama image memory 140-2-2 exists in the memory 140-2 in FIG. 1. As shown in FIG. 11, the panorama input image memory stores data of an image having a height of 1 to PH and a width of 1 to PW. The details of the process in step 951 will be described hereinlater with reference to FIG. 14. The panorama image data stored in the panorama image memory 140-2-2 is converted into an image display signal and the image display signal is displayed on the panorama image display window 320. At this time, the cursor 322 as information regarding the current position and direction of the probe 200 is also displayed on the panorama image display window 320.

In step 960, whether the save button 336 is pushed or not is checked. When YES, the routine advances to step 961. Step 961 relates to a panorama image storing process for storing the panorama image data generated and stored in the panorama image memory 140-2-2 into the external storage 190.

In step 970, whether the print button 337 is pushed or not is checked. When YES, the routine advances to step 971. Step 971 relates to a panorama image printing process for outputting the panorama image generated and stored in the panorama image memory 140-2-2 to the printer 180

In step 980, whether the setup button 333 is pushed or not is checked. When YES, the routine advances to step 981. Step 981 relates to a parameter setting process used to set a specific area 312 and an image synthesizing area 313 or to enter various information such as the region to be diagnosed and the name of the patient.

Finally, in step 990, whether or not the operation correction button 335 is pushed in the state where the panorama image formation is interrupted, that is, the variable "status" is 2 is checked. When YES, in step 991, the position of the cursor 322 which is currently displayed is shifted and displayed in a designated position. That is, while the button 335-1 is continuously pushed, the cursor sequentially returns to the position of the panorama image. When the button 335-2 is continuously pushed, the cursor is moved in the opposite direction. In such a manner, during the panorama image formation, the panorama image is corrected. By repeating the processes from step 915 to step 991, the panorama image from ultrasound images is formed in a state desired by the operator.

Figure 12:
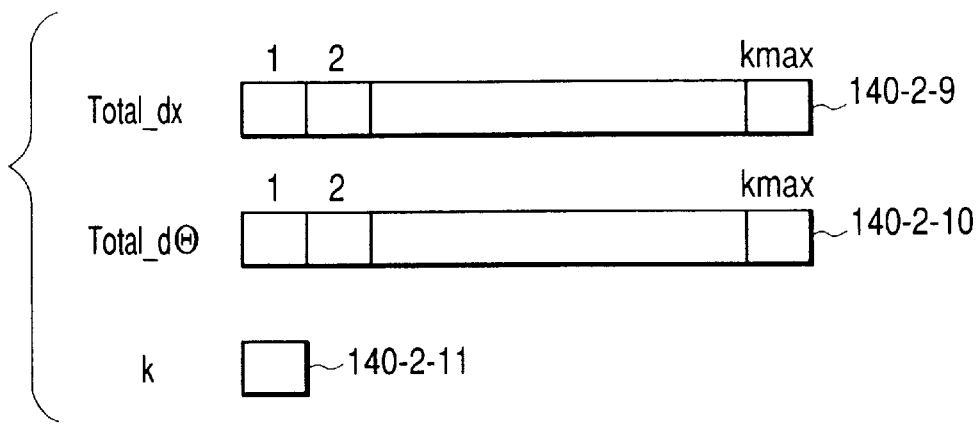
FIG. 12 is a diagram for explaining the structure of control data referred to by the control program executed in the panorama image synthesizing method of the invention.
Figure 13:
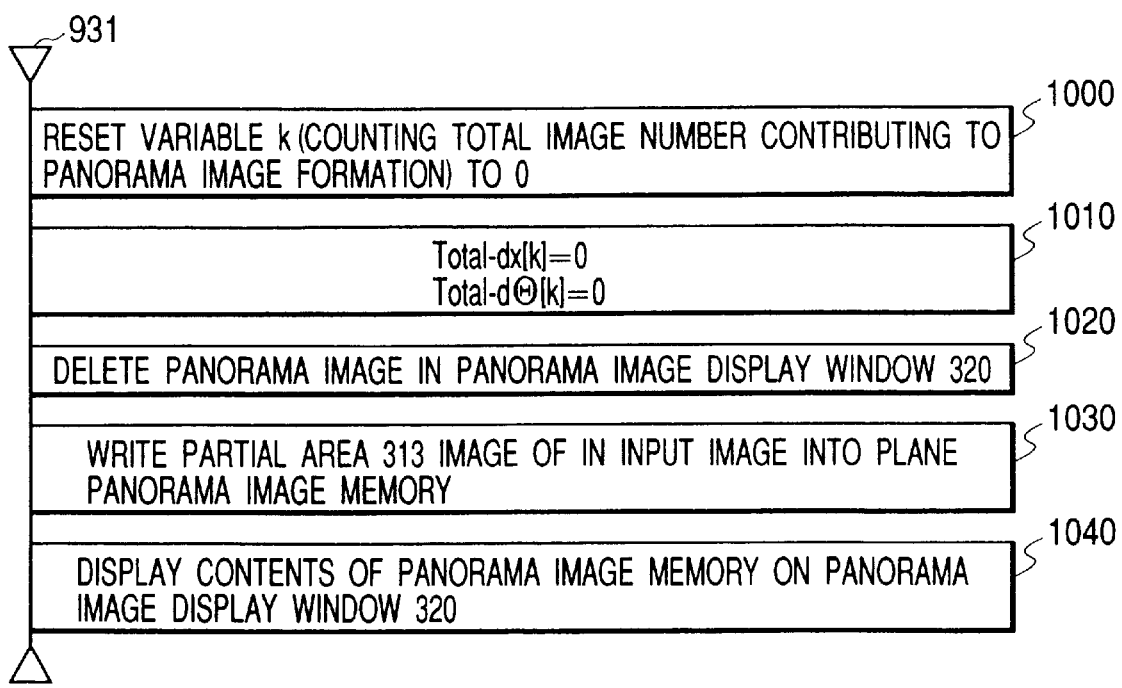
FIG. 13 is a flowchart showing the details of a panorama image generation starting process 931 in FIG. 10.

FIG. 13 is a flowchart showing the details of the panorama image formation starting process 931 in FIG. 10. First, in step 1000, a variable (k) for counting the total number of motion image frames contributed to the panorama image formation is reset to 0. The variable (k) is stored in the memory 140-2-11 in FIG. 12. In step 1010, the element at the head 1 of each of the memory area Total_dx 140-2-9 and the memory area Total_dΘ 140-2-10 in which the shift and rotation parameters used to form the panorama image are stored is reset to 0 (FIG. 12). In step 1020, the panorama image 321 which is being displayed on the panorama image display window 320 is deleted.

In step 1030, the input image data in the partial area 313 is written into a plane panorama image memory 140-2-2 for storing the panorama image. The first frame image serves as a reference image when panorama images are formed. The shift parameter and the rotation parameter of each of subsequent frame images are expressed as a relative difference from the first frame image. In step 1040, the data in the panorama image memory 140-2-2 is displayed in the panorama image display window 320 and the cursor 322 is also displayed.

Figure 14:
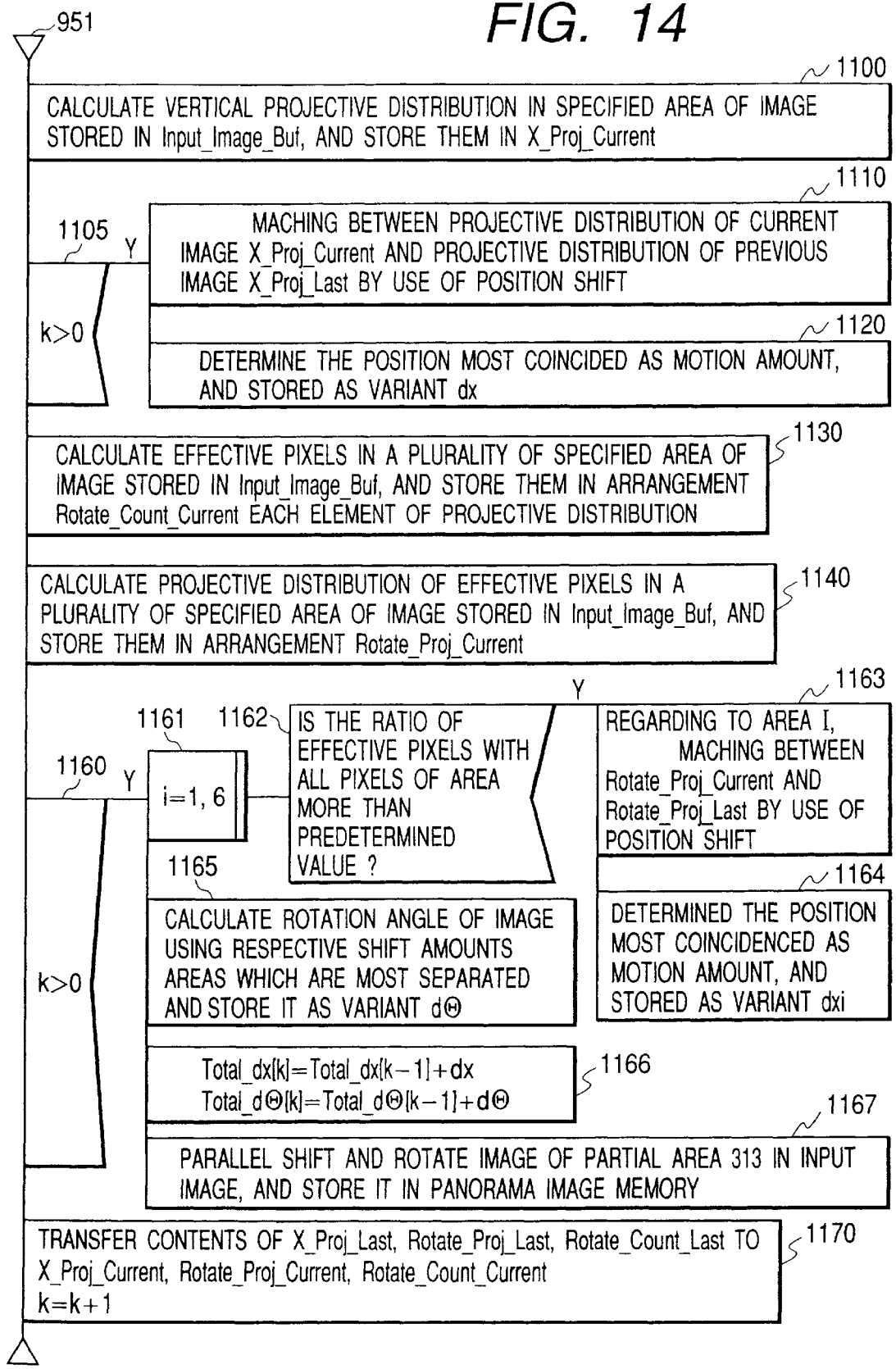
FIG. 14 is a flowchart showing the details of a panorama image generating process 951 in FIG. 10.

FIG. 14 is a flowchart showing the details of the panorama image forming process 951 in FIG. 10. Steps 1100 to 1120 relate to processes for obtaining the shift amount dx between consecutive frame images.

First, in step 1100, the vertical projection distribution in the specified area 312 of the image stored in the input image memory 14-2-1 is calculated and the result is stored in the memory area X_Proj_Current 140-2-3. In step 1105, whether the total frame number k is larger than 0 or not is determined. When YES, the routine advances to steps 1110 and 1120. In step 1110, matching, that is, similarity calculation is performed between the projective distribution of the current input image in the memory area 140-2-3 and the immediately preceding image projective distribution in the memory area Proj_Last 140-2-4 while shifting the position dx. In step 1120, the position dx most coincided is determined as the motion amount between two time-sequential images. As the matching, specifically, the above-mentioned equation (1) is calculated.

Steps 1130 to 1165 relate to processes to obtain the rotation amount dΘ between consecutive frame images.

In step 1130, the number of effective pixels in the plurality of partial areas 700i of an image stored in the input image memory 140-2-1, that is, the pixels in the gray portion 802 in which the ultrasound echoes exist are counted every row in each of the areas 700i and written in the memory area Rotate_proj_Current 140-2-6. In step 1140, the vertical projective distribution of the effective pixels in each of the plurality of partial areas 700i of the image stored in the input image memory 140-2-1 is calculated and written into the memory area Rotate_Proj_Current 140-2-5. Although the value of the projective distribution can be usually calculated by adding the values in each row, in this case, the value normalized by the number of effective pixels in each row is stored in a matrix.

In step 1160, whether the frame total number (k) is larger than 0 or not is checked. When YES, steps 1161 to 1167 are executed. In steps 1161 to 1164, a local shift amount between consecutive frame images is calculated with respect to the six areas 700i (i=1 . . . 6) First, in step 1162, whether the ratio of the effective pixels in the area (i) is equal to or higher than a predetermined value such as 0.5. When YES, steps 1163 and 1164 are executed. In step 1163, the matching is performed between the projective distribution of the currently input image in the memory area Rotate_Proj_Current 140-2-5 and the immediately preceding input image projective distribution in the memory area Rotate_Proj_Current 140-2-7 while shifting the position dxi. In step 1164, the position dxi which is the most coincided is determined as the shift amount in the area (i) between two time-sequential images.

In step 1165, the rotation amount dΘ is calculated by the equation shown in FIG. 8 from the shift amount between the areas which are most apart from each other among the areas in which the shift amounts can be calculated.

By the above processes, the shift amount dx and the rotation amount dΘ between neighboring frame images are obtained. In step 1166, the shift amount and the rotation amount between the reference image and the current image are calculated. They can be easily calculated by accumulating the shift amount and the rotation amount of the frame calculated this time to the calculation results of the preceding images. In step 1167, since the shift amount and the rotation amount of the current image are known with respect to the reference image, coordinate conversion based on the rotation amount and the shift amount is performed. The resultant image data is written to the panorama image memory 140-2-2. By the processes, the panorama image is formed from the sequence of frame images accompanying the shift and rotation.

Finally, in step 1170, preparation for the next panorama image formation is made. The data in the memory area X_Proj_Current 140-2-3 is transferred to the memory area X_Proj_Last 140-2-4, the data in the memory area Rotate_Proj_Current 140-2-5 is transferred to the memory area Rotate_Proj_Last 140-2-7, and the data in the memory area Rotate_Proj_Current 140-2-6 is transferred to the memory area Rotate_Count_Last 140-2-8. Only 1 is added to the variable (k) for counting the total frame images used for the panorama image formation.

As described above, according to the panorama image forming method of the invention, the shift amount and the rotation amount between images are detected with respect to only the effective pixels. Consequently, even when the part such as bone or cavity which dos not transmit the ultrasound pulses is included in an image obtained during the diagnosis, it can be prevented that the part exerts an influence on the detection result. Since the projective distribution over a wide area is used as an image characteristic amount, the shift amount and the rotation amount can be stably detected from an ultrasound image having much noise. Further, the calculation amount of the projective distribution used to detect the shift amount and the rotation amount is extremely small. Consequently, an effect such that the calculation can be executed in a real time manner by a cheap CPU is produced.

Although the method and apparatus of the invention for synthesizing a panorama image from ultrasound images have been described by the embodiment of the ultrasound diagnosing device, the invention is not limited to the embodiment. When the position of the generation source of the motion image fluctuates, obviously, the invention can be applied to the case where a sequence of frame images is synthesized to obtain a synthetic image. Although the case where the probe, ultrasound transmitter, and ultrasound imaging unit and a computer unit such as CPU are integrally connected has been described as the embodiment, the case where a series of frame images are stored in an image accumulating memory, and the image data in the image accumulating memory is inputted to obtain the panorama image is also included.

According to the invention, when it is applied to the ultrasound diagnosing device or the like, motion images captured during diagnosis are automatically synthesized to thereby form the panorama image. The panorama image can be formed in a real time manner from the sequence of slice images obtained by the probe operation of the operator of the device. The forming state of the panorama image can be checked momentarily on the display and an erroneous probe operation during the diagnosis can be corrected. Since the probe and the display are integrated in the preferred embodiment, the operator can perform the diagnosing work without turning his/her eyes off from the diagnostic region. As described above, according to the invention, the ultrasound diagnosing device of high operability can be realized.

While the present invention has been described above in conjunction with the preferred embodiments, one of ordinary skill in the art would be enabled by this disclosure to make various modifications to this embodiment and still be within the scope and spirit of the invention as defined in the appended claims.

What is claimed is:

1. A method of synthesizing a panorama image from ultrasonic images, comprising:
    a step of obtaining data of a plurality of consecutive ultrasound frame images constructing an ultrasound motion image;
    a step of obtaining a shift amount of a specific area of the plurality of consecutive ultrasound frame images by use of correlation of a characteristic amount derived from said specific area of the plurality of consecutive ultrasound frame images;
    a step of obtaining a rotation amount of the specific area of the consecutive ultrasound frame images by use of distributions of shift amounts, each of which is derived from a difference between the characteristic amount of corresponding partial areas obtained by dividing each of the consecutive ultrasound frame images in one axis direction;
    a step of detecting positional relation data between the plurality of consecutive ultrasound frame images by use of the shift amount and rotation amount; and
    a step of connecting the plurality of ultrasound frame images by using the positional relation data to synthesize panorama image data.

2. The method of synthesizing a panorama image from ultrasound images according to claim 1, further comprising a step of displaying the panorama image data on a display of a display device.

3. The method of synthesizing a panorama image from ultrasound images according to claim 1, wherein said characteristic amount is a projective distribution.

4. An apparatus for synthesizing a panorama image from ultrasound images by obtaining a sequence of a plurality of ultrasound frame images constructing an ultrasound motion image, detecting positional relation data between the plurality of frame images, and synthesizing panorama image data by using the positional relation data, comprising:
    an input unit of image data of the plurality of frame images;
    a calculating unit including a first signal processing means for obtaining a shift amount of a specific area of the plurality of consecutive ultrasound frame images by use of correlation of a characteristic amount derived from said specific area of the plurality of consecutive ultrasound frame images, and a second signal processing means for obtaining a rotation amount of the specific area of the consecutive ultrasound frame images by use of distributions of shift amounts, each of which is derived from a difference between the characteristic amount of corresponding specific partial areas obtained by dividing each of the consecutive ultrasound frame images in one axis direction; and
    means for synthesizing a panorama image from a plurality of frame images by using the shift amount and the rotation amount obtained by the calculating unit.

5. The apparatus for synthesizing a panorama image from ultrasound images according to claim 4, wherein said characteristic amount is projective distribution.

6. The apparatus for synthesizing a panorama image from ultrasound images according to claim 5, wherein each of the first and second signal processing means normalizes the projective distributions in the specific area and the plurality of specific partial areas by using a number obtained by integrating pixels in one axis direction.

7. The apparatus for synthesizing a panorama image from ultrasound images according to claim 6, wherein the pixel used for obtaining the projective distribution is a pixel of a specific color signal.

8. The apparatus for synthesizing a panorama image from ultrasound images according to claim 4, wherein the second signal processing means uses the shift amount obtained from the set of areas which are most apart from each other in the plurality of specific partial areas divided in one axis direction.

9. The apparatus for synthesizing a panorama image from ultrasound images according to claim 4, further comprising image displaying means for converting the motion image data and panorama image data into image display signals and displaying the signals on a display.

10. The apparatus for synthesizing a panorama image from ultrasound images according to claim 9, wherein the image displaying means displays an image process area as a figure for detecting at least one of the shift amount and the rotation amount in a motion image display area on the display.

11. The apparatus for synthesizing a panorama image from ultrasound images according to claim 9, wherein the image displaying means has process area designating means for displaying an image process area as a figure used to form the panorama image in a motion image display area on the display.

12. The apparatus for synthesizing a panorama image from ultrasound images according to claim 9, wherein the image displaying means has position designating means for displaying position information as a figure of a motion image which is currently being processed in the panorama image display area on the display.

13. The apparatus for synthesizing a panorama image from ultrasound images according to claim 9, wherein the image displaying means has means for returning the panorama image to a state at an arbitrary prior time by moving the position information.

14. The apparatus for synthesizing a panorama image from ultrasound images according to claim 4, wherein the input unit of data of the plurality of frame images is connected to a probe for obtaining ultrasound data, and the calculating unit, synthesizing means, and displaying means are constructed to display at least one of a motion image or the panorama image on the display simultaneously with the probe operation.

15. The apparatus for synthesizing a panorama image from ultrasound images according to claim 14, wherein the display is integrally formed with the probe.

16. The apparatus for synthesizing a panorama image from ultrasound images according to claim 14, wherein the probe is provided with means for instructing setup or reset of the probe operation.

17. The apparatus for synthesizing a panorama image from ultrasound images according to claim 4, further comprising detachable image storing means for storing the panorama image data.

18. An apparatus for synthesizing a panorama image from ultrasound images by obtaining data of a sequence of a plurality of ultrasound frame images, detecting positional relation data between the plurality of frame images, and synthesizing panorama image data by using the positional relation data, comprising:

an input unit of image data of the plurality of frame images;

a calculating unit including a first signal processing means for calculating a shift amount and a rotation amount of images in a specific area in the plurality of frame images from the image data;

a step of obtaining a shift amount of a specific area of the plurality of consecutive ultrasound frame images by use of correlation of a characteristic amount derived from said specific area of the plurality of consecutive ultrasound frame images, and a second signal processing means for obtaining a rotation amount of the specific area of the consecutive ultrasound frame images by use of distributions of shift amounts, each of which is derived from a difference between a characteristic amount of corresponding partial areas obtained by dividing each of the consecutive ultrasound frame images in one axis direction;

means for synthesizing a panorama image from the plurality of frame images by using the shift amount and the rotation amount obtained by the calculating unit; and a display for displaying the motion image and the panorama image by converting the motion image data and the panorama image data into image display signals, wherein an image operation type symbol display area having areas of a panorama instruction button, a reset button, and a forward/backward instruction button is provided in the display, and start of display, interruption, restart, or reversion of the panorama image is performed by the corresponding button in the instruction button area.

19. A recording medium which can be read by a computer and on which a program for obtaining a plurality of frame images constructing an ultrasound motion image, detecting positional relation data of the plurality of frame images, and connecting the plurality of frame images by using the positional relation data, thereby obtaining panorama image data, is recorded, wherein the program comprises:

a first step of calculating a projective distribution of pixels in the vertical direction in a specified area in each of present and previous two frame images from which the positional relation data is to be obtained, and obtaining a shift amount in the horizontal direction between the present and previous two frame images by matching the present and previous projective distributions;

a second step of providing a plurality of divided designated areas in corresponding positions in each of the present and previous two image frames from which the positional relation data is to be obtained, calculating the projective distribution of pixels in each of the plurality of divided designated areas, and matching the projective distributions in the plurality of divided designated areas, thereby obtaining a shift amount in each of the plurality of divided designated areas between the present and previous two frame images;

a third step of calculating a rotational angle between the present and previous two frame images by using the shift amount of each of the divided designated areas obtained in the second step; and a fourth step of shifting and rotating the image area to be synthesized in the present image frame by the shift amount obtained in the first step and the rotational angle obtained in the third step, and writing the result into a panorama image memory, the first to fourth steps being repeatedly executed on a newly input image frame as the present image frame.

20. The recording medium which can be read by a computer, according to claim 19, wherein in the second step, the ratio of effective pixels to all pixels in each of the plurality of divided partial areas is checked and, when the ratio is equal to or larger than a predetermined value, the projective distribution of the divided designated area is calculated, and the third step has a step of selecting the shift amount between two divided designated areas which are most apart from each other among the shift amounts of the plurality of divided partial areas, and a step of performing a calculation of $d\Theta = \tan^{-1}(dxa-dxb)/h$, where each of dxa and dxb denotes a shift amount between the two divided designated areas and $d\Theta$ denotes the rotational angle.

* * * * *